(12) United States Patent
Tanaka et al.

(10) Patent No.: US 6,991,623 B2
(45) Date of Patent: Jan. 31, 2006

(54) DISPOSABLE DIAPER

(75) Inventors: Yoshikazu Tanaka, Kagawa-ken (JP); Hirotomo Mukai, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 602 days.

(21) Appl. No.: 10/116,413

(22) Filed: Apr. 4, 2002

(65) Prior Publication Data

US 2002/0147438 A1 Oct. 10, 2002

(30) Foreign Application Priority Data

Apr. 6, 2001 (JP) .............................. 2001-109133

(51) Int. Cl.
*A61F 13/20* (2006.01)
(52) U.S. Cl. .......................... 604/385.29; 604/385.01; 604/397; 604/402
(58) Field of Classification Search .......... 604/385.29, 604/385.21–385.31, 385.01, 397, 393, 387, 604/400, 402
See application file for complete search history.

(56) References Cited

U.S. PATENT DOCUMENTS

| | | | | |
|---|---|---|---|---|
| 3,688,767 A | * | 9/1972 | Goldstein ................... 604/394 |
| 4,834,738 A | * | 5/1989 | Kielpikowski et al. 604/385.22 |
| 5,593,400 A | * | 1/1997 | O'Leary ................. 604/385.27 |
| 6,102,892 A | * | 8/2000 | Putzer et al. ........... 604/385.01 |
| 6,168,585 B1 | * | 1/2001 | Cesco-Cancian ....... 604/385.26 |
| 6,364,863 B1 | * | 4/2002 | Yamamoto et al. ..... 604/385.27 |
| 6,632,211 B2 | * | 10/2003 | Otsubo ................... 604/385.22 |
| 6,648,868 B2 | * | 11/2003 | Sayama et al. ......... 604/385.22 |
| 2002/0147439 A1 | * | 10/2002 | Tanaka et al. ............... 604/398 |
| 2003/0023220 A1 | * | 1/2003 | Ukegawa et al. ......... 604/385.3 |
| 2003/0125697 A1 | * | 7/2003 | Bushman et al. ...... 604/385.24 |
| 2003/0176846 A1 | * | 9/2003 | Karami ................... 604/385.29 |
| 2004/0002689 A1 | * | 1/2004 | Igaue et al. ............ 604/385.01 |
| 2004/0127880 A1 | * | 7/2004 | Weber ................... 604/385.22 |

FOREIGN PATENT DOCUMENTS

| | | |
|---|---|---|
| EP | 0 763 353 | 3/1997 |
| EP | 0 904 753 | 3/1999 |
| EP | 0 933 073 | 8/1999 |
| JP | 11-99165 | 4/1999 |

* cited by examiner

*Primary Examiner*—Tatyana Zalukaeva
*Assistant Examiner*—Ginger Chapman
(74) *Attorney, Agent, or Firm*—Butzel Long

(57) ABSTRACT

A disposable diaper includes a cover member having a front waist region, a back waist region, and a crotch region and a liquid-absorbent panel disposed inside the cover member. The panel is joined to the cover member on inner surfaces of the front and back waist regions by an elastic band which extends in an elastically contractible condition in a circumferential direction of a wearer's waist. At least a portion of a clearance existing between the cover member and the elastic band is closed by a sheet material having extensibility back and forth of the diaper.

3 Claims, 7 Drawing Sheets

DISPOSABLE DIAPER

BACKGROUND OF THE INVENTION

This invention relates to a disposable diaper for absorption and containment of body wastes.

Japanese Patent Application No. 1999-99165A discloses a disposable diaper. The diaper comprises a sheet-like cover member, and a liquid-absorbent member attached to an inner surface of the cover member by an elastic band, which extends in a circumferential direction of a wearer's waist.

The cover member comprises a front waist region, a back waist region, and a crotch region disposed therebetween. Contours of side edges provided in the crotch region are curved inward. When developed into a planar shape, the front and back waist regions and the crotch region take an hourglass shape. Of such a cover member, at least one of the front and back waist regions assumes elastic flexibility in the circumferential direction of the waist. The side edges of the front waist region of the cover member and the side edges of the back waist region of the same are connected together or formed so as to be connectable.

The liquid-absorbent member comprises a liquid-permeable top sheet disposed so as to face the skin of a wearer of the diaper, a liquid-impermeable back sheet disposed so as to face the cover member, and liquid-absorbent material disposed between both sheets. These sheets extend from the crotch region into the front and back waist regions on an inner side of the cover member.

In each of the front and back waist regions, the liquid-absorbent member has an elastic band extending in an extended state in the circumferential direction of the waist. Respective extremities of the elastic band that have extended in the circumferential direction of the waist are connected to respective side edges of the waist region in which the elastic band is placed. In a preferred mode of such a known diaper, the side edges of the front and back waist regions of the cover member are connected together, thereby defining a shape of a brief having a waist opening and a pair of leg openings.

In the case of the known diaper of brief type, when a mother helps an infant put on a diaper, its leg may often be erroneously inserted into a space between the cover member and the elastic member.

SUMMARY OF THE INVENTION

It is an object of this invention to solve such problems as possibly occurring is handling a disposable diaper made by prior arts.

According to this invention, there is provided a disposable diaper comprising a cover member which includes a front waist region, a back waist region and a crotch region, and a liquid-absorbent panel which includes a top sheet defining a body facing surface, a back sheet defining an opposite surface, and a liquid-absorbent core interposed therebetween and which extends between the front and back waist regions on an inner side of the cover member. The cover member is elastically constructible in a circumferential direction of a wearer's waist in at least one of the front and back waist regions. Side edges of the front and back waist regions of the cover member are in one of manners in which said edges are connected together and formed connectably. Longitudinally opposite ends of the liquid-absorbent panel are supported on inner surfaces of the front and back waist regions, wherein at least one of the longitudinally opposite ends of the panel is supported by joining to an elastic band extending in an elastically contractible condition in the circumferential direction of said at least one of the front and back waist regions (hereinafter referred to as "waist region"); and ends of the elastic band in the circumferential direction of the being secured to side edges facing the elastic band.

The diaper further comprising a sheet material which has a first portion and a second portion opposed to the first portion and is interposed between the elastic band and the waist region opposed to the elastic band, with the first portion connected to the waist region and the second portion connected to the elastic band, wherein the sheet material is extensible back and forth of the diaper between the waist region and the elastic band and at least partially closes a clearance which develops between the waist region and the elastic band.

DETAILED DESCRIPTION OF THE PREFERRED EMBODIMENTS

A disposable diaper according to the invention will be described in more detail hereinbelow by reference to the accompanying drawings.

Figure 1:
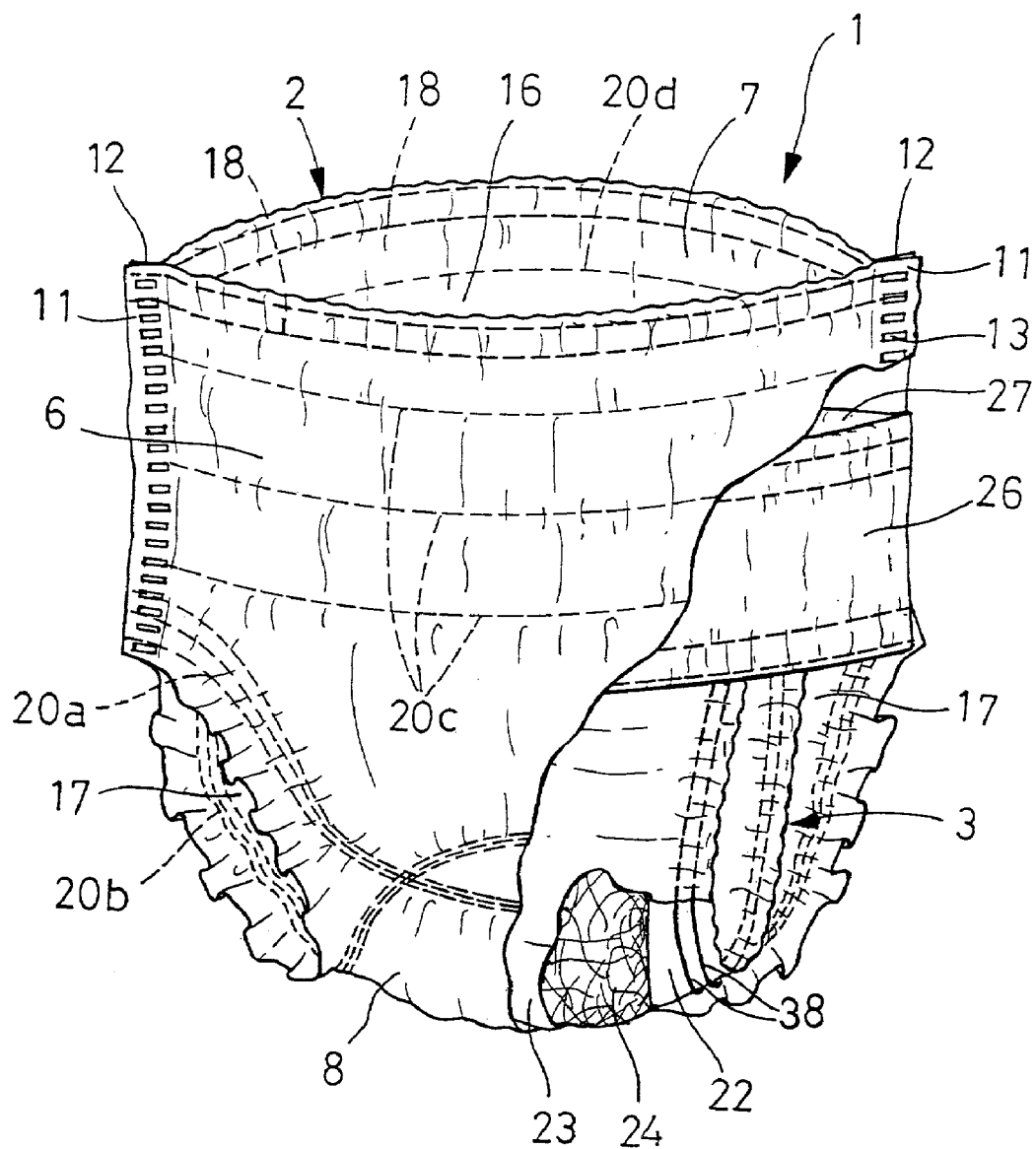
FIG. 1 is a partially cutaway perspective view of a diaper.

A disposable diaper 1 shown in FIG. 1 in a form of a partially cutaway perspective view has a cover member 2 formed into a shape of a brief, and a liquid-absorbent panel 3 disposed inside the cover member 2. The cover member 2 comprises a front waist region 6, a back waist region 7, and a crotch region 8 disposed between those regions 6, 7. Side edges 11 of the front waist region 6 and side edges 12 of the back waist region 7 are overlaid with each other and connected in joining regions 13 provided intermittently on each of the side edges in a longitudinal direction thereof, so as to prevent substantial separation thereof. The cover member 2 has a waist opening 16 and a pair of leg openings 17. A plurality of elastic strings 18 are provided along edge regions of the waist opening 16 in an extended condition, in other words, in an elastically contractible condition. A plurality of elastic strings 20a are provided in an elastically contractible condition along edge regions of the respective leg openings 17 so as to extend across the crotch region 8 toward the front waist region 6. Further, a plurality of elastic strings 20b are provided in an elastically contractible condition along the edge region of the respective leg openings 17 so as to extend across the crotch region 8 toward the back waist region 7. A plurality of elastic strings 20c are provided in the front waist region 6 in an elastically contractible condition parallel with each other to the longitudinal direction thereof. Further, a plurality of elastic strings 20d are provided in the backwaist region 7 in an elastically contractible condition state parallel with each other to the longitudinal direction thereof. In each of the front and back waist regions 6, 7, the number of elastic strings 18, 20c, and 20d extending in the circumferential direction of the waist can be increased or decreased, as required. Moreover, any of the elastic strings 18, 20c, and 20d corresponding to either of the front and back waist regions 6, 7, may be omitted so as to impart flexibility to only one of the front and back waist regions 6, 7 in the circumferential direction of the waist.

The liquid-absorbent panel 3 has a liquid-permeable top sheet 22, a liquid-impermeable back sheet 23, and liquid-absorbent core 24 interposed therebetween. The panel 3 extends to both the front and back waist regions 6, 7 from the crotch region 8 of the cover member 2 as the center of its extensions. The panel 3 is joined to an inner surface of a front elastic band 26 which extends in an elastically contractible condition in the circumferential direction of the waist in the front waist region 6. Further, the panel 3 is joined to an inner surface of a back elastic band 27 which extends in an elastically contractible condition in the circumferential direction of the waist in the back waist region 7. Respective ends of the front elastic band 26 in the circumferential direction of the waist integrally connected with the front waist region 6 in the joining regions 13. Similarly, respective ends of the back elastic band 27 in the circumferential direction of the waist are integrally connected with the back waist region 7, in the joining regions 13. In the side edges of the panel 3, a plurality of elastic strings 38 extend in an elastically contractible condition along the side edges of the liquid-absorbent core 24.

Figure 2:
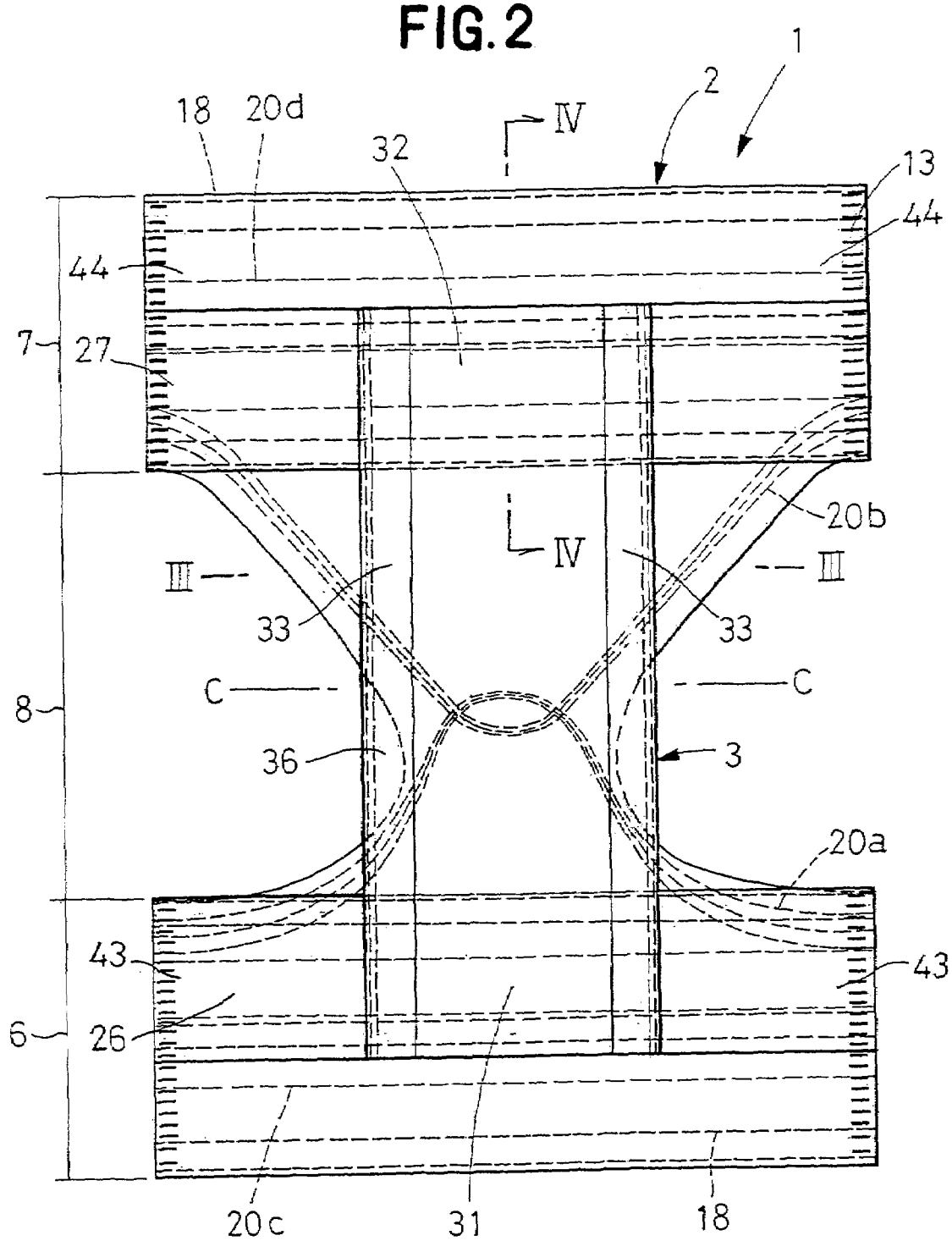
FIG. 2 is a view of the diaper shown in FIG. 1 when developed.
Figure 3:
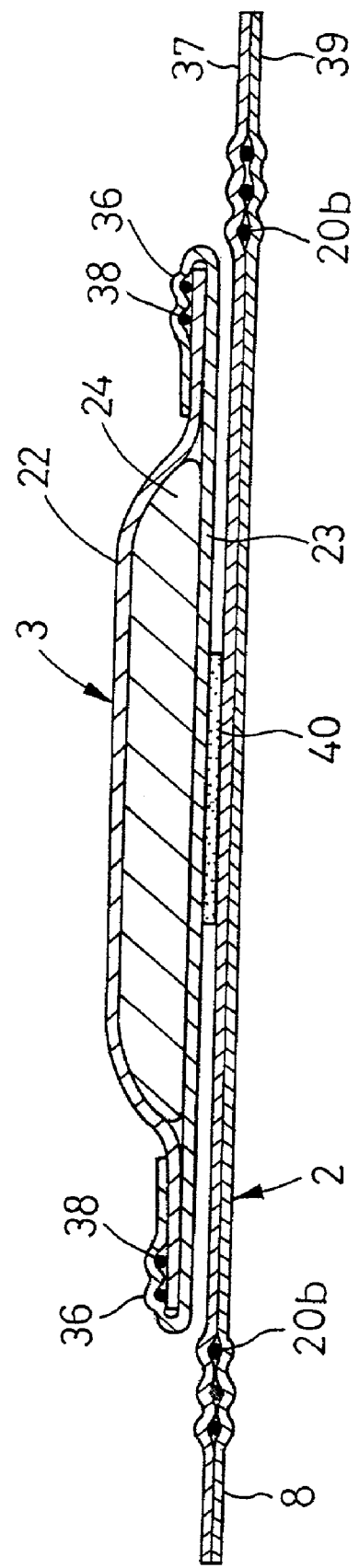
FIG. 3 is a cross-sectional view taken along line III—III shown in FIG. 1.

FIG. 2 is a partially cutaway plan view of the diaper 1 when longitudinally developed after separating in the front and back waist regions 6, 7 of the cover member 2 in the joining regions 13 shown in FIG. 1. FIG. 3 is a cross-sectional view of the diaper 1 taken along a line III—III in FIG. 2. The illustrated liquid-absorbent panel 3 assumes a substantially rectangular shape elongated in the longitudinal direction thereof. The panel 3 has a front edge region 31, a back edge region 32, and side edge regions 33. Extensions of the top and back sheets 22, 23 of the panel 3 extending beyond the outer edge of the substantially-rectangular-shaped liquid-absorbent core 24 are overlapped with each other and are joined together by means of bonding or welding as is shown in FIG. 3. In each of the side edges 33, the back sheet 23 extends laterally beyond its corresponding edge of the top sheet 22, and the extending portion is folded over the top sheet 22. The extensions of the top and back sheets 22, 23 forms a side flap 36. A plurality of elastic strings 38 are provided in the space defined between the folded portion of the back sheet 23 and the top sheet 22. The elastic strings 38 are secured to an inner surface of at least one of the top and back sheets 22, 23 in an elastically contractible condition in the longitudinal direction of the panel 3 (i.e., the vertical direction to the plane of the drawing in FIG. 3). The center portion of the panel 3 in a transverse direction thereof is joined to the center portion of the crotch region 8 of the cover member 2 in a transverse direction, by means of an adhesive 40.

The front and back elastic bands 26, 27—which extend in the circumferential direction of the waist (i.e., the horizontal direction in the drawing in FIG. 2) in the front and back waist regions 6, 7—are expanded in the circumferential direction of the waist. Side edges 43, 44 of the front and back waist regions 6, 7 in the circumferential direction of the waist are joined to the inner surfaces of the side edges of the cover member 2 in the joining regions 13, respectively. The front and back elastic bands 26, 27 are spaced away at equal distance from the center line C—C dividing the diaper 1 into equal halves in its longitudinal direction. When the diaper 1 shown in FIG. 2 is folded along the center line C—C and assembled into a state shown in FIG. 1, the edges 43 of the front waist region 6 overlap the edges 44 of the back waist region 7. Thereby, the elastic bands 26, 27 form a loop inside the cover member 2.

The cover member 2 is formed by joining an inner sheet 37 and an outer sheet 39 together through bonding or welding. The elastic strings 18, 20a, 20b, 20c, and 20d are secured to the inner surfaces of the sheets 37, 39 by means of an adhesive. A permeable or impermeable, nonwoven or woven fabric or a plastic film can be used for the two sheets 37, 39.

Figure 4:
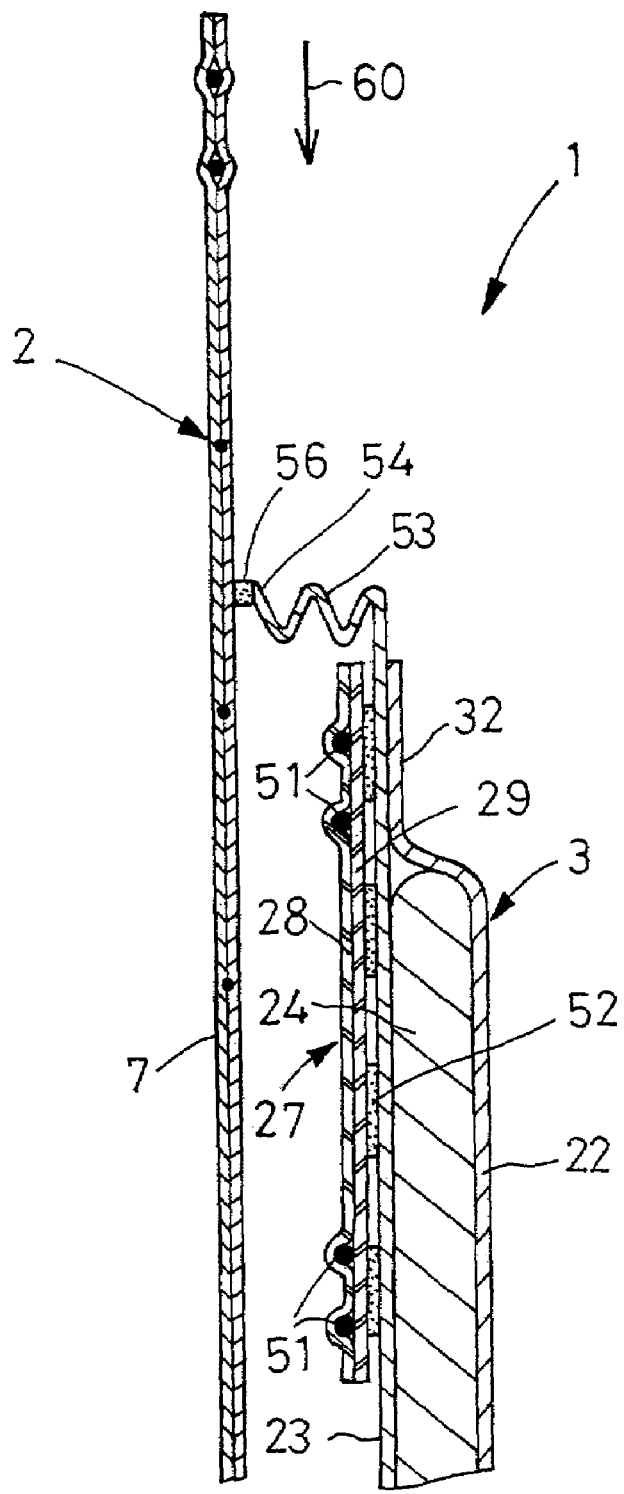
FIG. 4 is a cross-sectional view taken along line IV—IV shown in FIG. 1.

FIG. 4 is a cross-sectional view taken along line IV—IV shown in FIG. 2. The back elastic band 27 is formed by overlaying two nonwoven fabrics 28, 29 one on top of the other and joining the fabrics together through bonding or welding. A plurality of elastic strings 51 extending in the circumferential direction of the waist are secured to the inner surfaces of the nonwoven fabrics 28, 29 in an elastically contractible condition. Thus, the elastic strings 51 extend and contract in the circumferential direction of the waist. The back edge region 32 of the panel 3 is joined to the inner surface of the back elastic band 27 by an adhesive 52. The back sheet 23 of the panel 3 has an extending region 53 which extends upward beyond the band 27. The extending section 53 creates gathers in a space between the inner surface of the cover member 2 and the band 27. An edge region 54 is joined to the cover member 2 by an adhesive 56. Preferably, the extending region 53 is folded regularly into a Z- or W-shape, thus creating gathers. Such back elastic band 27 may also comprise an elastic sheet such as a rubber sheet in place of an illustrated example. The front elastic band 26 is formed in the same manner as the back elastic band 27.

When the diaper 1 is worn, the position of the cover member 2 assembled into a shape of a brief is maintained by means of the elastic strings 18, 20a, and 20b provided along the edges of the waist and leg openings 16, 17, and the elastic strings 20c and 20d provided in the front and waist regions 6, 7. The position of the panel 3 is maintained by means of the front elastic band 26 and the back elastic band 27. By means of an action of the elastic strings 38 provided along the side edges of the panel 3, the panel 3 is closely contacted with a groin region or leg regions. Even when the cover member 2 is moved in association with a movement of the wearer's waist or legs, the panel 3 still remains closely contacted with the wearer's skin by way of the front elastic band 26 and the back elastic band 27, which are substantially independent of the cover member 2. Therefore, the diaper 1 is not influenced by the movement of the cover member 2 and remains as it is with respect to the wearer's body. So long as the panel 3 of the diaper 1 is worn with its surface adequately fit to the wearer's body in the beginning, the panel 3 can be maintained in that state for a long period of time and is excellent in its function of preventing leakage of exudates. When the diaper 1 is worn, the movement of the leg inserted into the diaper in the direction of an arrow 60 shown in FIG. 4 is hindered by the extending region 53 of the panel 3, thus an entry of the leg into a space between the cover member 2 and the back elastic band 27 is obstructed. By means of the gathers constituted by the extending region 53, the extending region 53 possesses extendability with respect to inward and outward directions of the diaper 1. Hence, the movement of the cover member 2 is not transmitted to the back elastic band 27 by way of the extending region 53.

Although not illustrated, a relationship between the cover member 2, the panel 3, and the front elastic band 26 is identical with that shown in FIG. 4. Moreover, the movement of the cover member 2 is not transmitted to the panel 3 even in the front waist region 6. When the diaper 1 is worn, his/her legs do not enter the space between the cover member 2 and the front elastic band 26.

Figure 5:
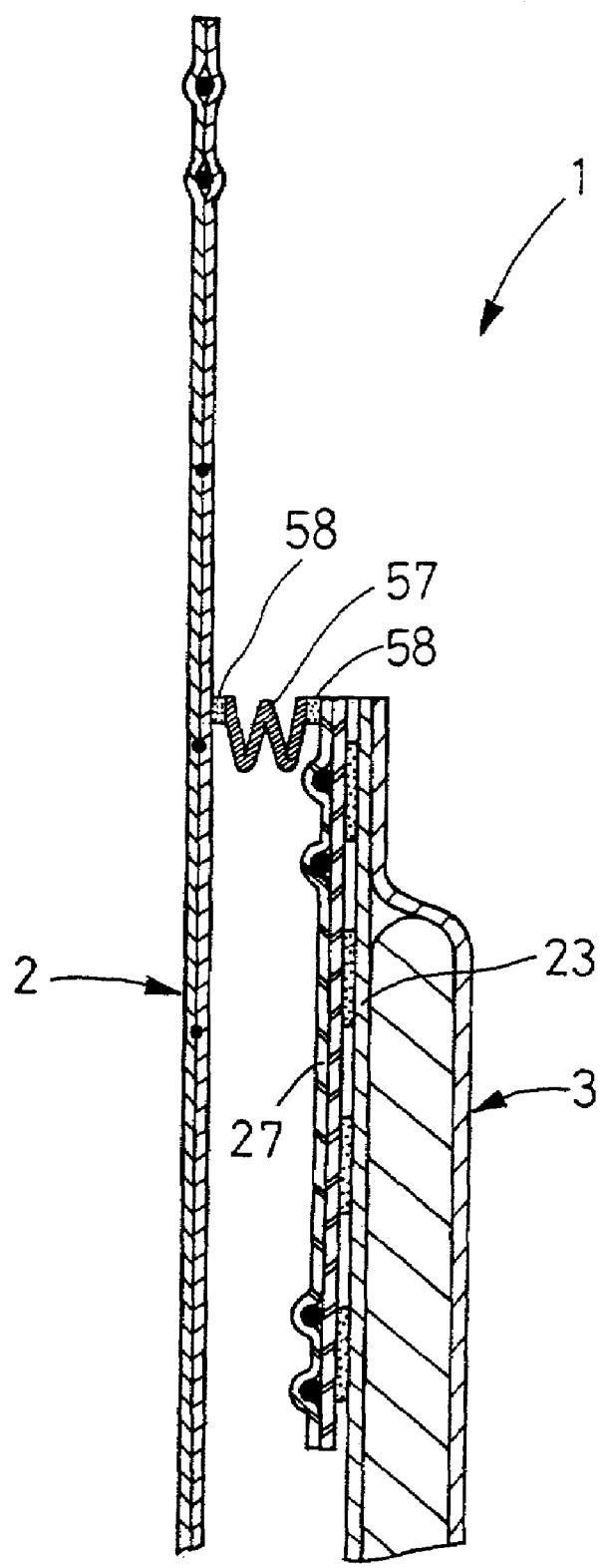
FIG. 5 is a view similar to FIG. 4, showing another embodiment of the invention.

FIG. 5 is a cross-sectional view similar to that shown in FIG. 4, showing another embodiment of the invention. In relation to the diaper 1, as shown in FIG. 4, a sheet 57 different from the back sheet 23 is interposed between the inner surface of the cover member 2 and the back elastic band 27, instead of making the back sheet 23 of the panel 3 to extend from the back elastic band 27. The sheet 57 is attached to the cover member 2 and the back elastic band 27 by an adhesive 58. In case the sheet 57 is not elastically extensible, the sheet 57 is preferably folded into a w-shape as illustrated, thus creating gathers. In contrast, in a case where the sheet 57 is elastically extensible and can extend and contract toward inside and outside directions of the diaper 1, gathers can be omitted. The sheet 57 may also be provided over the entire length of the elastic band 27 in the circumferential direction of the waist. Alternatively, the sheet 57 may be provided in a portion of the entire length of the elastic band 27. If the sheet 57 is breathable, the sheet 57 serves to prevent the wearer's waist from becoming hot and stuffy, as flow of air within the cover member 2 is not obstructed.

Figure 6:
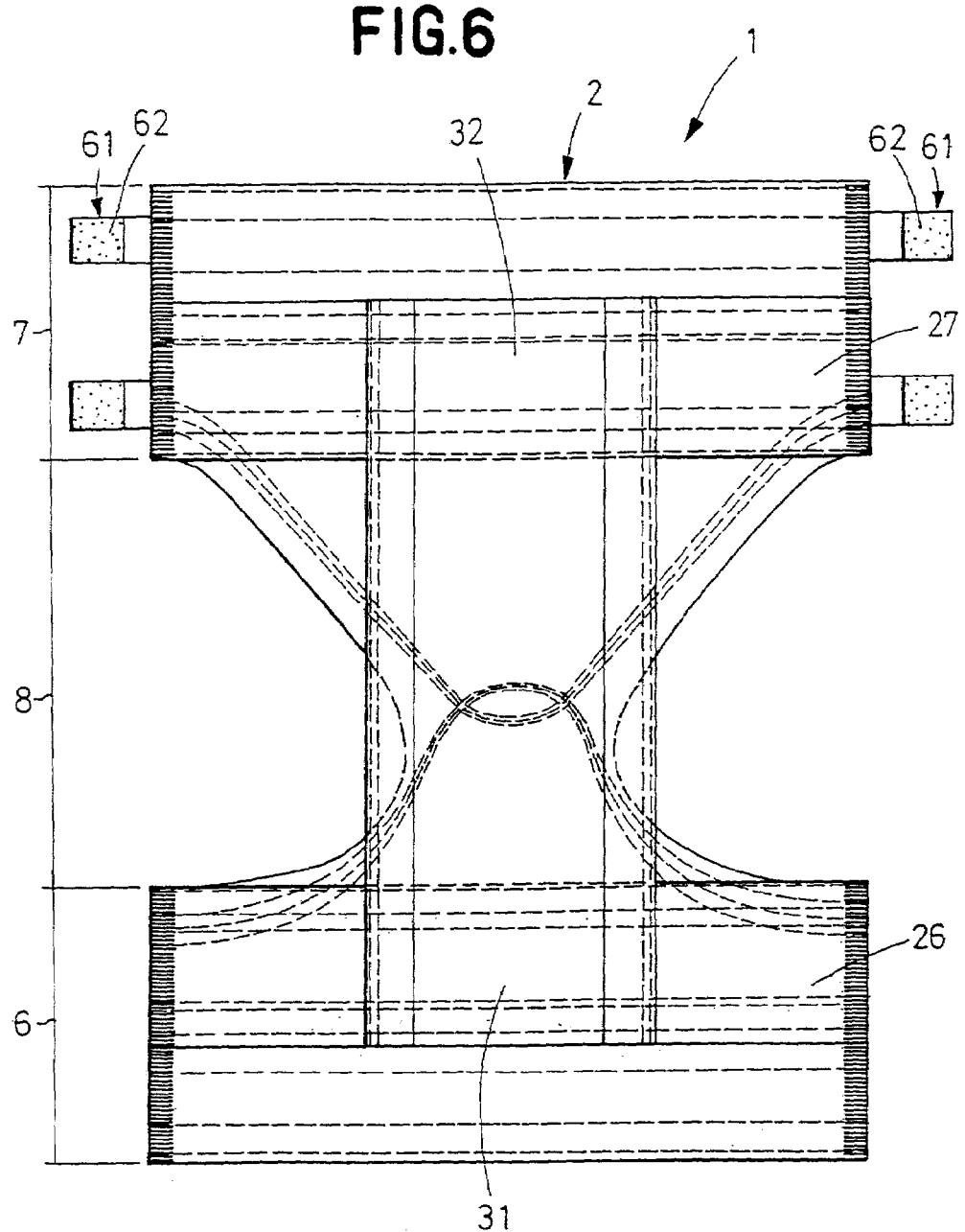
FIG. 6 is a plan view of a diaper according to still another embodiment of the invention.

FIG. 6 is a plan view of the diaper 1 according to still another embodiment of the present invention. This diaper 1 is an open type and assumes substantially the same plane geometry as that of the diaper 1 shown in FIG. 2. The diaper 1 shown in FIG. 6, however, has tape fasteners 61 provided on respective side edges of the back waist region 7, wherein each of the tape fasteners 61 is coated with an adhesive 62. When the diaper 1 is worn, the fasteners 61 are affixed to the outer surface of the front waist region 6, thereby connecting the side edges 43 of the front waist region 6 and the side edges 44 of the back waist region 7 in a removable manner. The sheet 57 shown in FIG. 5—which extends over substantially the entire length of the elastic bands 26, 27—is provided between the back elastic band 27 and the cover member 2 as well as between the front elastic band 26 and the cover member 2. Such diaper 1 prevents a mother or a nurse who handles it from accidentally inserting her hand into a space between the cover member 2 and the front or back elastic band 26 or 27.

Figure 7:
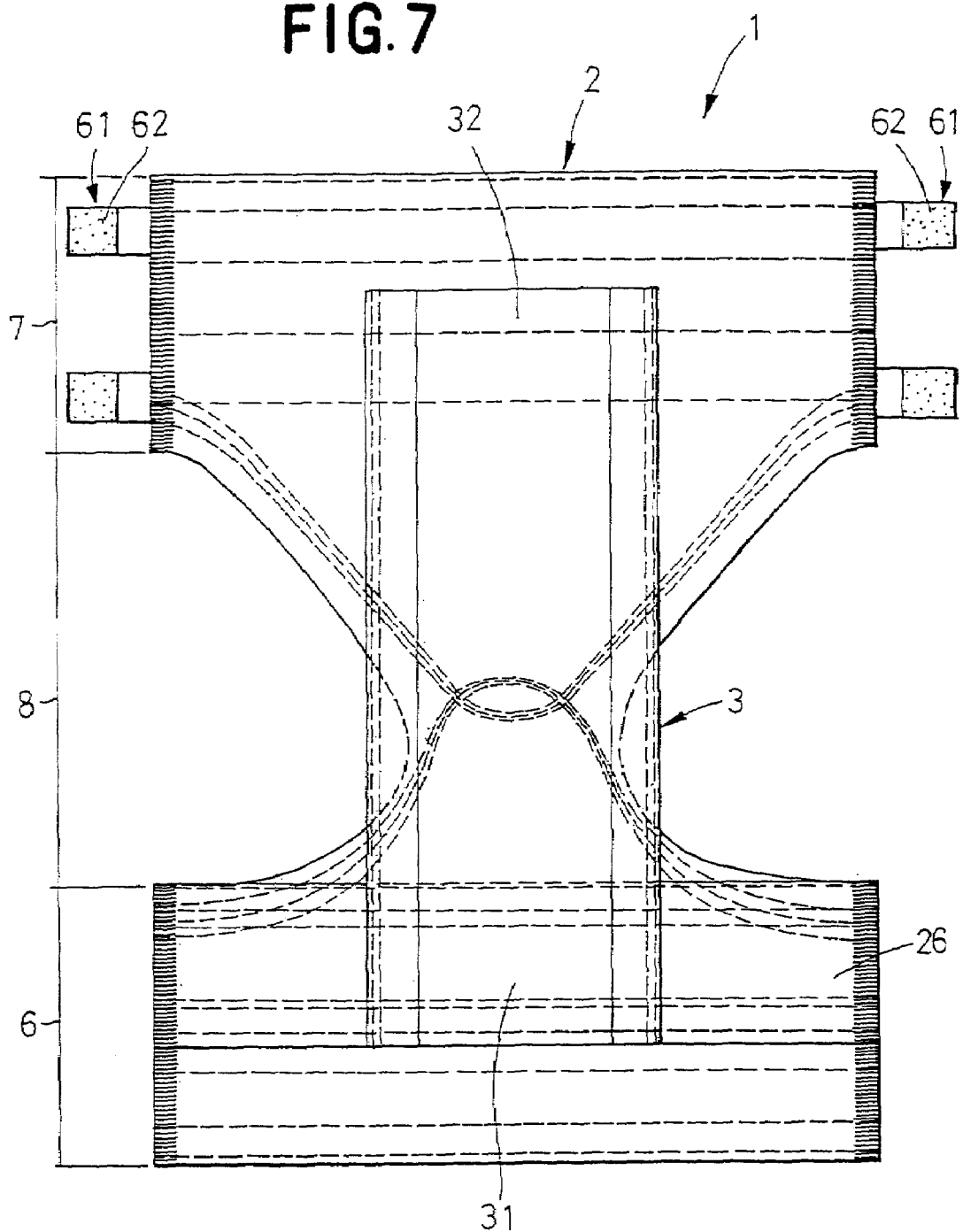
FIG. 7 is a view similar to FIG. 6, showing yet another embodiment of the invention.

FIG. 7 is also a view similar to FIG. 6, showing yet another embodiment of the invention. In contrast with the diaper 1 shown in FIG. 6, the diaper 1 has the back edge region 32 of the panel 3 joined to the inner surface of the back waist region 7 through bonding or welding. Further, the front edge region 31 is joined to the front elastic band 26 in the same manner as shown in FIG. 6. In the diaper 1 according to the invention, only one of the elastic bands 26 and 27 corresponding to the front waist region 6 or to the back waist region 7 of the cover member 2 may be provided, and the panel 3 may be bonded directly to the other region of the cover member 2. Even in an example shown in FIG. 7, the clearance existing between the cover member 2 and the elastic band 26 or 27 must be closed with the back sheet 23 of the panel 3 or the sheet 57 shown in FIG. 5.

In relation to a disposable diaper according to the invention, a cover member and a liquid-absorbent panel are attached together by an elastic band which is provided on the cover member and elastically extends and contracts in the circumferential direction of the waist. The clearance existing between the cover member and the elastic band is closed by a sheet elastically extensible toward inside and outside directions of the diaper. Hence, there is no fear of a wearer's leg or hand being accidentally inserted into the clearance between the cover member and the elastic band.

What is claimed is:

1. A disposable diaper comprising:
   a cover member which includes a front waist region, a back waist region and a crotch region;
   a liquid-absorbent panel which includes a top sheet defining a body facing surface, a back sheet defining an opposite surface and a liquid-absorbent core interposed therebetween and which extends between the front and back waist regions on an inner side of the cover member;
   the cover member being elastically contractible in a circumferential direction of a wearer's waist in at least one of the front and back waist regions;
   side edges of the front and back waist regions of the cover member being connected together;
   longitudinally opposite ends of the liquid-absorbent panel being supported on inner surfaces of the front and back waist regions;
   an elastic band extending in an elastically contractible condition in the circumferential direction joining at least one of the longitudinally opposite ends of the panel to at least one of the front and back waist regions, said elastic band being joined to the at least one of the longitudinally opposite ends of the panel at least at one point between the liquid-absorbent core and the cover member where the elastic band longitudinally overlaps a portion of the liquid-absorbent core and
   ends of the elastic band in the circumferential direction are secured to side edges facing the elastic band;
   the diaper further comprising:
   a sheet material having a first portion and a second portion opposed to the first portion which sheet material is interposed between the elastic band and a waist region opposed to the elastic band, with the first portion connected to the cover member at the waist region and the second portion connected to the elastic band, wherein the sheet material is extensible back and forth of the diaper between the waist region and the elastic band and at least partially closes a clearance which develops between the waist region and the elastic band.

2. The diaper according to claim 1, wherein said sheet material includes gathers formed therein which cause said sheet material to be extensible.

3. The diaper according to claim 1, wherein said sheet material comprises an elastically extensible sheet.

* * * * *